US012575813B2

(12) United States Patent
Yeo et al.

(10) Patent No.: US 12,575,813 B2
(45) Date of Patent: Mar. 17, 2026

(54) CERVICOVAGINAL FLUID COLLECTION DEVICE

(71) Applicants: Singapore Health Services Pte Ltd, Singapore (SG); MAP Plastics Pte Ltd, Singapore (SG)

(72) Inventors: Seow Heong George Yeo, Singapore (SG); Wee Hong Edwin Thia, Singapore (SG); Tai Wai Yeo, Singapore (SG); Vijayavel Thangavel, Singapore (SG); Qi Hong Yao, Singapore (SG)

(73) Assignees: Singapore Health Services Pte Ltd, Singapore (SG); MAP Plastics Pte Ltd, Singapore (SG)

( * ) Notice: Subject to any disclaimer, the term of this patent is extended or adjusted under 35 U.S.C. 154(b) by 882 days.

(21) Appl. No.: 17/597,466

(22) PCT Filed: Jul. 9, 2020

(86) PCT No.: PCT/SG2020/050393
§ 371 (c)(1),
(2) Date: Jan. 6, 2022

(87) PCT Pub. No.: WO2021/010893
PCT Pub. Date: Jan. 21, 2021

(65) Prior Publication Data
US 2022/0265250 A1     Aug. 25, 2022

(30) Foreign Application Priority Data

Jul. 12, 2019     (SG) ............................. 10201906515Y

(51) Int. Cl.
*A61B 10/00*          (2006.01)

(52) U.S. Cl.
CPC ..................... *A61B 10/0045* (2013.01); *A61B 2010/0074* (2013.01)

(58) Field of Classification Search
CPC ................... A61B 10/0045; A61B 2010/0074
See application file for complete search history.

(56) References Cited

U.S. PATENT DOCUMENTS 9,658,125 B2     5/2017   Gilbert et al.
2006/0071000 A1  4/2006   Weist et al.
(Continued)

FOREIGN PATENT DOCUMENTS

CN          1493506 A      5/2004
CN          106264623 A    1/2017
(Continued)

OTHER PUBLICATIONS

International Search Report issued for International Patent Application No. PCT/SG2020/050393, dated Oct. 16, 2020 in 3 pages.
(Continued)

*Primary Examiner* — Daniel L Cerioni
(74) *Attorney, Agent, or Firm* — Knobbe, Martens, Olson & Bear, LLP

(57)          ABSTRACT

A cervicovaginal fluid collection device includes a generally tubular housing. A first end of the housing includes an enclosed tip and through holes provided at the enclosed tip. A probe is provided within the housing. A first end of the probe is provided with a screw-like structure. The screw-like structure has a sliding fit with an inner bore of the housing. At least a first end of the screw-like structure is provided at the enclosed tip of the housing. A fluid-absorbing swab is provided on the probe within the housing adjacent a second end of the screw-like structure to absorb fluid drawn into the housing. Rotation of the screw-like structure relative to the housing draws fluid that is adjacent and exterior to the (Continued)

enclosed tip of the housing into the housing through at least one of the through holes.

14 Claims, 5 Drawing Sheets

(56) References Cited

U.S. PATENT DOCUMENTS

| | | | |
|---|---|---|---|
| 2007/0270715 A1 | 11/2007 | Ng | |
| 2008/0045986 A1 | 2/2008 | To et al. | |
| 2009/0050648 A1 | 2/2009 | Wisniewski | |
| 2011/0056982 A1 | 3/2011 | Swanick | |
| 2011/0087133 A1* | 4/2011 | Ching | A61B 10/02 |
| | | | 600/572 |
| 2015/0168244 A1 | 6/2015 | Gilbert et al. | |
| 2015/0297196 A1* | 10/2015 | Ching | A61B 10/0045 |
| | | | 600/572 |
| 2016/0030020 A1 | 2/2016 | Buurstede et al. | |

FOREIGN PATENT DOCUMENTS

| | | | |
|---|---|---|---|
| CN | 206020107 | U | 3/2017 |
| CN | 206082581 | U | 4/2017 |
| CN | 107343802 | A | 11/2017 |
| CN | 207085952 | U | 3/2018 |
| CN | 108349635 | A | 7/2018 |
| CN | 109913354 | A | 6/2019 |
| DE | 10 2009 053 341 | B3 | 7/2011 |
| WO | 2014082159 | A1 | 6/2014 |
| WO | 2018/091906 | A1 | 5/2018 |

OTHER PUBLICATIONS

Written Opinion issued for International Patent Application No. PCT/SG2020/050393, dated Oct. 14, 2020 in 4 pages.

International Preliminary Report on Patentability issued for International Patent Application No. PCT/SG2020/050393, mailed Jan. 27, 2022 in 6 pages.

Office Action issued in Chinese Application No. 2020800506549, dated Jan. 27, 2025.

Search Report issued in Chinese Application No. 2020800506549, dated Jan. 27, 2025.

* cited by examiner

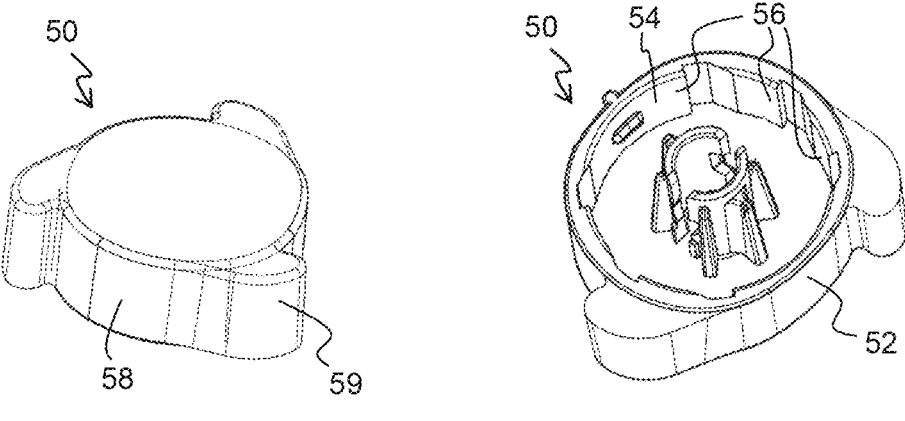
Fig. 4                              Fig. 5
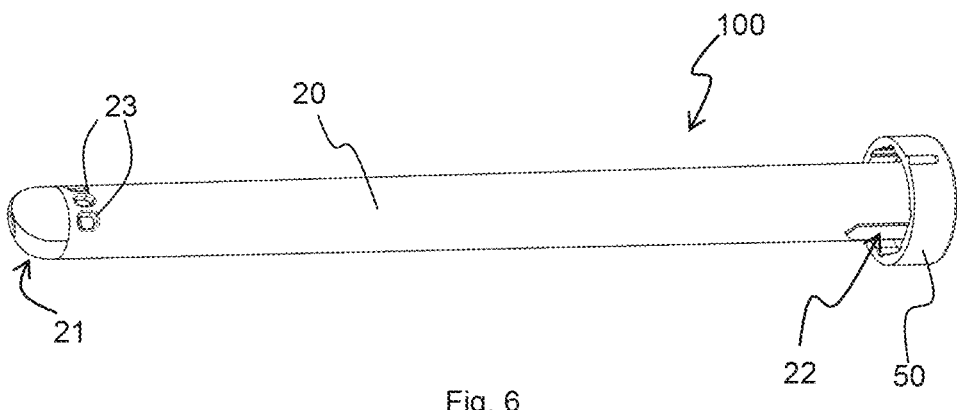
Fig. 6
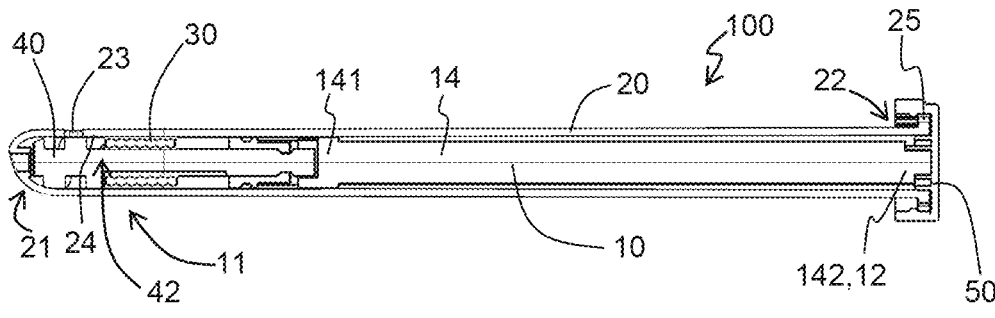
Fig. 7

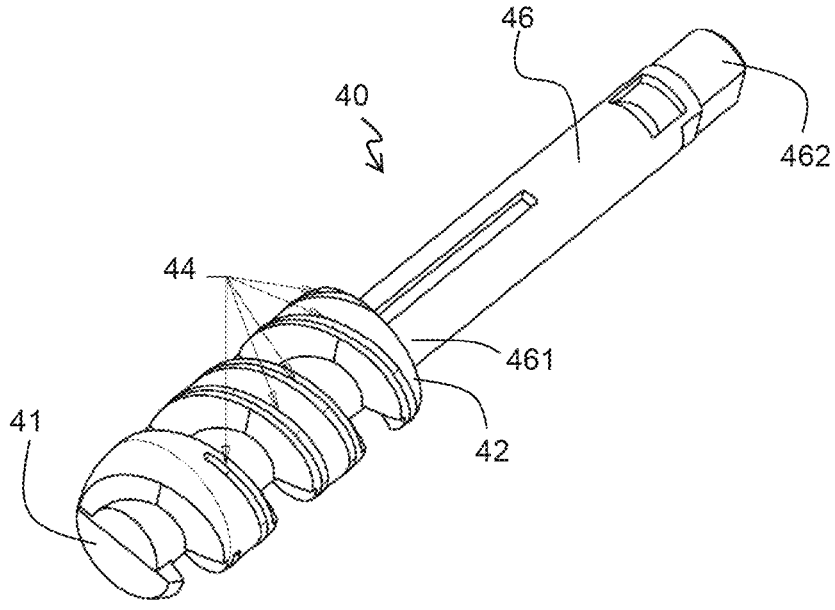
Fig. 10
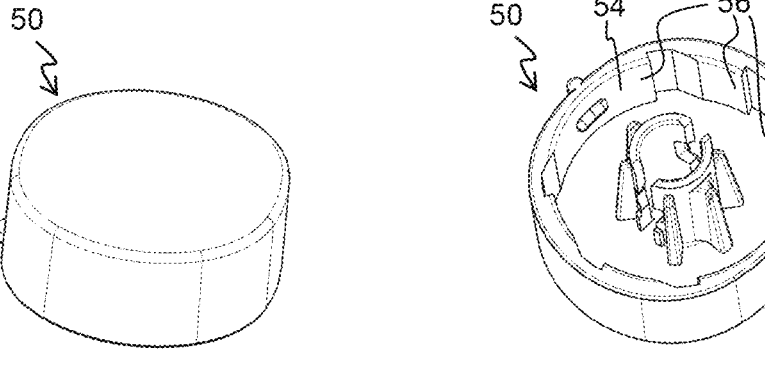
Fig. 11                  Fig. 12

CERVICOVAGINAL FLUID COLLECTION DEVICE

CROSS-REFERENCE TO RELATED APPLICATIONS

This application is the U.S. National Phase under 35. U.S.C. § 371 of International Application PCT/SG2020/050393, filed Jul. 9, 2020, which claims priority to Singapore patent application Ser. No. 10/201,906515, filed Jul. 12, 2019. The disclosures of the above-described applications are hereby incorporated by reference in their entirety.

FIELD

This invention relates to a cervicovaginal fluid collection device.

BACKGROUND

The current protocol for collection of cervicovaginal secretion uses a speculum to open the walls of the vagina and a cotton swab inserted through the speculum to swab the cervix or vagina and obtain a secretion sample. This current protocol has multiple issues. Firstly, sample contamination through vulval or skin contact may occur during swab insertion and removal. Secondly, application of the speculum is invasive and is generally uncomfortable and embarrassing for the patient. Thirdly, it is time consuming for the healthcare provider. Therefore, it is desirable at times to be able to obtain a vaginal swab in a way that minimizes invasiveness to the patient while avoiding sample contamination.

The vagina is a long muscular tube-like part of the female anatomy extending from the cervix to the labia minora. Vaginal secretion is often produced by the vaginal lining and from the cervical canal glands. This cervicovaginal secretion is often collected as part of an obstetrics and gynecology examination. The collection of the cervicovaginal fluid (CVF) is, therefore, a common procedure and the collected CVF is used for analysis in clinical screening or investigations. For example, the presence of the phosphorylated isoform of insulin-like growth factor binding protein-1 (phIGFBP-1) in CVF is used as an indicator for imminent delivery in preterm delivery in pregnant patients [Paternoster et al. (2009), Phosphorylated insulin-like growth factor binding protein-1 in cervical secretions and sonographic cervical length in the prediction of spontaneous preterm delivery, Ultrasound Obstet Gynecol. 34:437-40]. The collected CVF can also be used to test for the presence of candidiasis infection, bacterial vaginosis and Trichomonas vaginalis, among other conditions.

The collection of CVF is currently usually performed in a clinic by a licensed medical practitioner using a speculum (FIG. 14, prior art) and a cotton swab (FIG. 15, prior art). The duck beak-like parts of the speculum are inserted into the vagina of the patient and used for dilation by moving apart the walls of the vagina for examination of the vagina and cervix. The cotton swab is then inserted through the speculum to swab the cervix and/or vagina for collection of CVF. The swab is then sealed in a container and transported to the laboratory for indicated assays.

It is currently challenging for medical personnel to obtain useful cervical material due to the flimsy nature of the cotton bud swap. More importantly, cervical materials collected by the swab are often brushed off from the cotton bud during the insertion and removal process. This is due to the muscular nature of the vaginal walls, as the vaginal cavity is normally closely sealed by the lower and upper walls. In addition, the usage of a vaginal speculum is considered by the patients to be generally uncomfortable and invasive. It is also well-acknowledged that the procedure is often embarrassing for the patient. In addition, the procedure is time-consuming for the medical practitioner and takes up clinic time. Furthermore, the current cotton swab is flimsy and can be challenging for the medical practitioner to collect the required sample. Lastly, contamination of the swab can occur during the swab insertion and removal as a result of unintentional contact with the vaginal wall, vulva or skin, leading to delays, inaccurate results being obtained, or even a repeat of the procedure being required.

It is therefore desirable at times to be able to obtain CVF in a way that minimizes invasiveness to the patient and reduces procedural time while avoiding sample loss and/or contamination.

SUMMARY

According to a first aspect, there is provided a cervicovaginal fluid collection device comprising: a generally tubular housing, a first end of the housing comprising an enclosed tip and a number of through holes provided at the enclosed tip; a probe provided within the housing, a first end of the probe provided with a screw-like structure, the screw-like structure having a sliding fit with an inner bore of the housing, at least a first end of the screw-like structure provided at the enclosed tip of the housing; and a fluid-absorbing swab provided on the probe within the housing adjacent a second end of the screw-like structure to absorb fluid drawn into the housing; wherein rotation of the screw-like structure relative to the housing draws fluid that is adjacent and exterior to the enclosed tip of the housing into the housing through at least one of the through holes; and wherein fluid drawn into the housing is absorbed by the fluid-absorbing swab.

The screw-like structure may comprise a helical structure wrapped around a central shaft.

The crests of the helical structure may form a fluid-seal with the inner bore of the housing.

The enclosed tip may have a rounded configuration.

The probe may be removable from the housing and insertable into a conventional centrifuge tube to allow collection of the cervicovaginal fluid from the fluid-absorbing swab into the centrifuge tube.

The probe may be provided with a breakable portion provided between the fluid-absorbent swab and a second end of the probe for shortening the probe by breaking the probe at the breakable portion to allow complete insertion and sealing of the shortened probe within the conventional centrifuge tube.

The device may further comprise a cap in fixed connection with a second end of the probe, the cap provided outside a second end of the housing to facilitate rotation of the probe to rotate the screw-like structure relative to the housing.

The fixed connection may comprise a snap-fit joint allowing the cap to be detached from the second end of the probe.

The cap may enclose the second end of the housing and may be in rotatable engagement with the housing.

The cap and the housing may be configured to allow the rotatable engagement in only a specific direction dependent on direction of twist of the helical structure around the central shaft.

The second end of the housing may comprise a lip having a number of angled teeth to serve as a ratchet and an inner surface of a generally cylindrical wall of the cap may be provided with a number of angled protrusions to serve as pawls that engage the ratchet.

The cap may comprise a number of protruding stops provided on an outer surface of a generally cylindrical wall of the cap.

The cap may be provided with an extension cup offset from a main body of the cap enclosing the second end of the housing.

BRIEF DESCRIPTION OF FIGURES

In order that the invention may be fully understood and readily put into practical effect, there shall now be described by way of non-limitative example only exemplary embodiments of the present invention, the description being with reference to the accompanying illustrative drawings.

FIG. 4 is a perspective top view of a cap of the device of FIG. 1.

FIG. 5 is a perspective underside view of the cap of FIG. 4.

FIG. 6 is a perspective view of a second exemplary embodiment of the CVF collection device.

FIG. 7 is a longitudinal cross-section view of the device of FIG. 6.

FIG. 10 is a perspective view of a screw-like structure of the device of FIG. 6.

FIG. 11 is a perspective top view of a cap of the device of FIG. 6.

FIG. 12 is a perspective underside view of the cap of FIG. 11.

DETAILED DESCRIPTION

Figure 1:
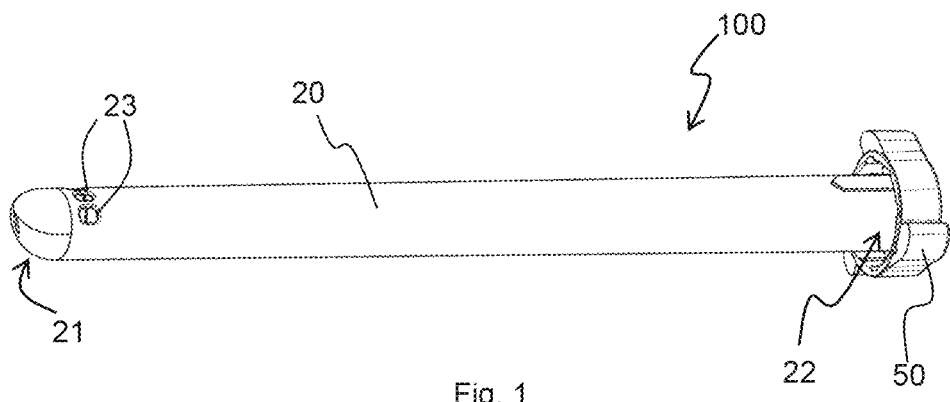
FIG. 1 is a perspective view of a first exemplary embodiment of a CVF collection device.

Exemplary embodiments of a cervicovaginal fluid (CVF) collection device 100 will be described below with reference to FIGS. 1 to 13. The same reference numerals are used across the figures to refer to the same or similar parts.

The presently disclosed CVF collection device 100 provides a simple and minimally-invasive method for sampling CVF. In order to achieve accurate test results, it is essential that a swab used to collect the CVF thereon is shielded from the vaginal wall during the insertion and removal from the vaginal cavity. To achieve this, the device 100 comprises a probe 10 that is enclosed by a cylinder or generally tubular housing 20, as shown in FIGS. 1-2 and 6-8. The housing 20 has an enclosed tip at a first end 21 and an open top or second end 22. The housing 20 is open at the second end 22 for the cotton swab 30 and probe 10 to be fitted into the housing 20. The enclosed tip 21 preferably has a rounded configuration for comfortable, non-damaging insertion into the vagina. A number of openings or through holes 23 are provided at or adjacent the enclosed tip 21 of the housing 20 from which CVF fluid can enter the housing 20 and be absorbed by the fluid-absorbing swab 30. The number of through holes 23 may be one or more as may be desired, for example, three, and edges of the through holes 23 are preferably rounded or smoothened to avoid scratching the vaginal walls. In exemplary embodiments, the housing 20 is preferably straight, may have a length of about 15 cm, may have an outer diameter of about 11 mm and a wall thickness of about 1 mm. Within the housing 20 is the probe 10 that stays completely within the housing 20 and does not protrude out of the tip 21 of the housing 20.

Figure 2:
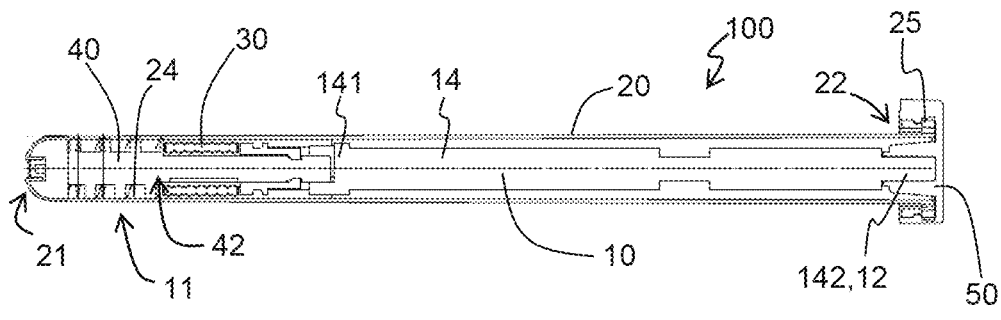
FIG. 2 is a longitudinal cross-section view of the device of FIG. 1.
Figure 3:
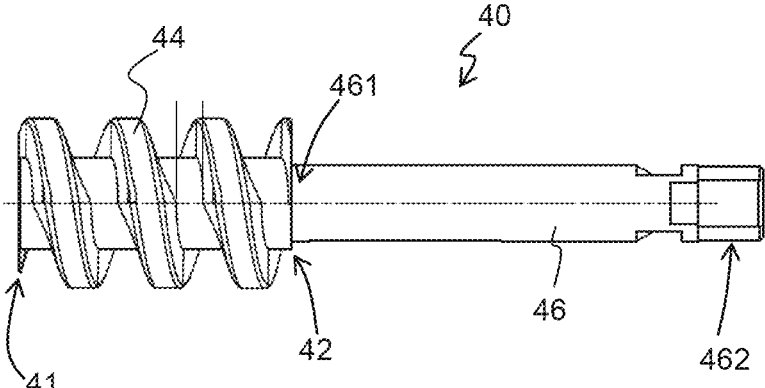
FIG. 3 is a perspective view of a screw-like structure of the device of FIG. 1.

The fit of the probe 10 in the housing 20 is such that rotation of the probe 10 within the housing 20 can be done with light finger force, but it is not free rotation and the probe 10 will not slip out of the housing 20 when device 100 is held inverted. To achieve this, the first end 11 of the probe 10 is provided with a screw-like structure 40 (as can be seen in FIGS. 2, 3, 7 and 10) that has a sliding fit with an inner bore 24 of the housing 20 as shown in FIGS. 2 and 7. At least a first end 41 of the screw-like structure 40 is provided at the enclosed tip 21 of the housing 20. The screw-like structure 40 comprises a helical structure 44 wrapped around a first end 461 of a central shaft 46 like a screw thread, wherein crests of the helical structure 44 effect the sliding contact with the inner bore 24 of the housing 20. In a preferred embodiment, the crests of the helical structure 44 may effect a fluid seal with the inner bore 24 of the housing 20 The central shaft 46 has a longitudinal axis that is colinear with a longitudinal axis of the probe 10 and a longitudinal axis of the housing 20. The rest of the probe 10 preferably comprises a rigid support shaft 14. A second end 462 of the central shaft 46 is connected to a first end 141 of the support shaft 14 while a second end 142 of the support shaft 142 (that forms the second end 12 of the probe 10) extends to at least the second end 22 of the housing 20 when the probe 10 is assembled with the housing 20, if not beyond. In an exemplary embodiment, the shaft 14 may have a diameter of about 7 mm and a length of about 12 mm while the screw-like structure 40 has a length of about 4 to 5 cm and a widest diameter that provides a sliding fit with the inner bore of the housing 20.

The fluid-absorbing swab 30 is provided adjacent the first end 11 of the probe 10 within the housing 20, preferably adjacent a second end 42 of the screw-like structure 40, as shown in FIGS. 2 and 7. Fluid that is adjacent and exterior to the enclosed tip 21 of the housing 20 is drawn into the housing 20 through at least one of the through holes 23 when the screw-like structure 40 is rotated relative to the housing 20 by rotating the probe 10 relative to the housing 20 in a specific direction. In some embodiments, the size of each through hole 23 is preferably not larger than the pitch of the helical structure 44 of the screw-like structure 40, and the number of through holes 23 are preferably provided as close to the most distal turn of the helical structure 44 as possible. Rotation of the screw-like structure 40 will generate a slight suction force, through Archimedes Principle, to draw the CVF that is adjacent and exterior to the enclosed tip 21 of the housing 20 into the housing 20 through at least one of the through holes 23 at the tip 21 of the housing 20. The specific direction of rotation depends on the handedness of the screw-like structure 40 in order for the screw-like structure to act as an Archimedes Screw inside the housing 20, and CVF that enters the housing 20 is drawn up the screw-like structure 40 as the screw-like structure 40 rotates, to be absorbed by the cotton swab 30. The draw of the CVF is achieved through both Archimedes Principle and the absorbent nature of the cotton swab 30. It is important that the draw of fluid is an active process. Without this active process, there would be no take up of fluid.

As shown in FIGS. 1, 2, 6, 7 and 13, the probe 10 may be topped off by a cap 50 provided at the second end 12 of the probe 10, wherein the cap 50 encloses a second end 22 of the housing 20, and wherein the cap 50 serves to facilitate rotation of the probe 10 relative to the housing 20 in order to rotate the screw-like structure 40. Various embodiments of the cap 50 are shown in FIGS. 4, 5, and 11-13. In some embodiments, the cap 50 may be fixedly connected to the second end 142 of the shaft 14 of the probe 10 via a snap-fit joint to allow the cap 50 to be detached or broken away from the probe 10 by hand. The cap 50 may preferably also engage the second end 22 of the housing 20 while attached to the second end 12 of the probe, as can be seen in FIGS. 2 and 7.

Figures 8, 9:
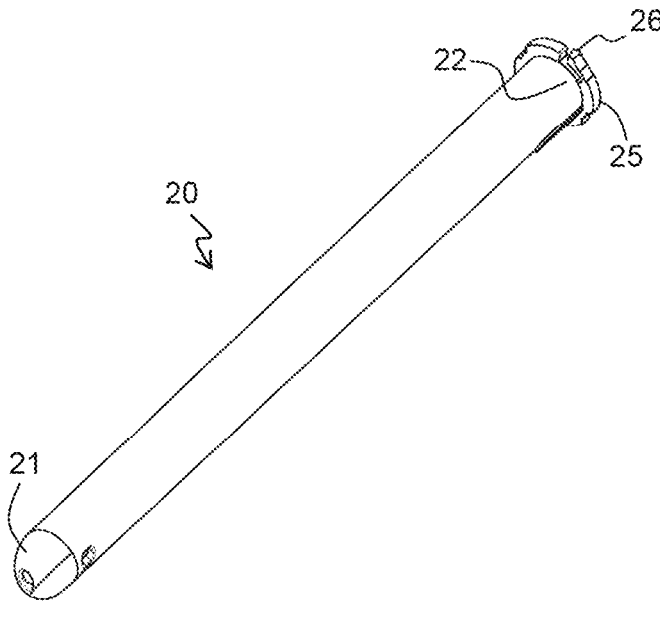
FIG. 8 is a perspective view of a housing of the device of FIG. 6.
FIG. 9 is a perspective view of a support shaft of a probe of the device of FIG. 6.

As mentioned above, depending on the handedness or direction of twist of the helical structure 44 of the screw-like structure 40 on the central shaft 46, only a specific direction of rotation of the screw-like structure 40 relative to the housing 20 will result in fluid uptake through the number of through holes 23. Thus, if a cap 50 is provided on the device 100, to ensure a correct direction of rotation of the screw-like structure 40 relative to the housing 20 during use, the cap 50 is preferably configured to be rotatable relative to the housing 20 only in a specific direction that, according to the handedness of the screw-like structure 40, will result in fluid being moved along the screw-like structure 40 towards the swab 30 when the cap 50 is rotated in the specific direction. For example, the second end 22 of the housing may comprise a lip 25 having a number of angled teeth 26 (one or more) as shown in FIG. 8 to serve as a ratchet while an inner surface 54 of a generally cylindrical wall 52 of the cap 50 may be provided with a number of angled protrusions 56 to serve as pawls, as shown in FIGS. 5 and 12, that engage the ratchet and prevent rotation of the cap 50 relative to the housing 20 in a first direction while allowing rotation of the cap 50 relative to the housing 20 in a second direction.

Figure 13:
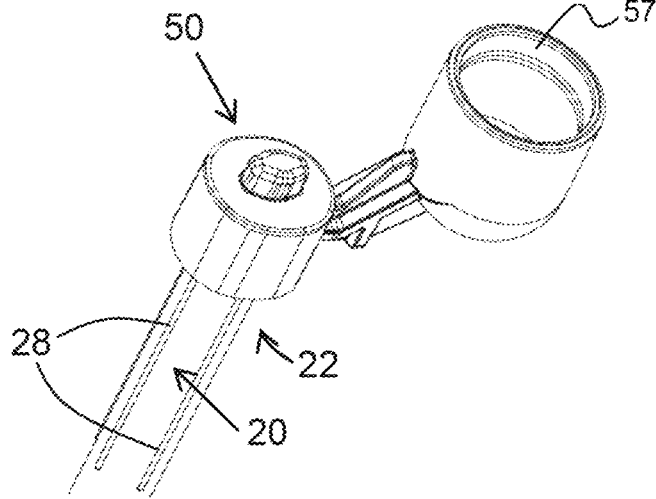
FIG. 13 is a perspective truncated view of a third exemplary embodiment of the CVF collection device.
Figure 14:
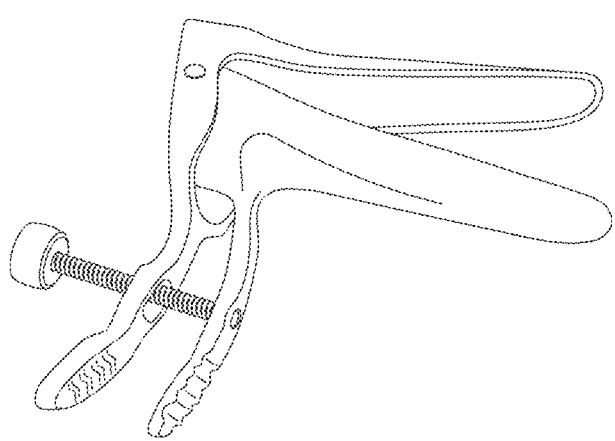
FIG. 14 (prior art) is a photograph of single-use speculum.
Figure 15:
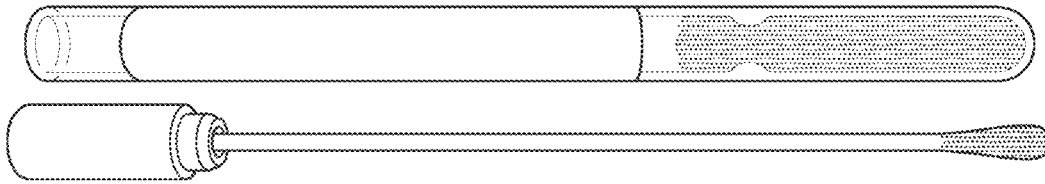
FIG. 15 (prior art) is a photograph of a single-use gynaecological cotton swab with case.

Naturally, the allowed direction of rotation will be the specific direction of rotation of the screw-like structure 40 that causes fluid to be drawn into the housing 20 through the number of through holes 23 when the screw-like structure 40 is rotated in the allowed direction relative to the housing 20. Accordingly, where the device 100 is provided with a cap 50, an outer surface 58 of the wall 52 of the cap 50 may optionally be provided with one or more protruding stops 59 to facilitate rotation of the cap 50 by hand in the allowed direction, as shown in FIG. 5. Alternatively, as shown in FIG. 13, the cap 50 may be provided with an extension cup 57 that is offset from the main body of the cap 50 that encloses the second end 22 of the housing 20. The extension cup 57 serves as a finger rest to facilitate rotation of the cap 50 relative to the housing 20.

During use, the device 100 is inserted into the vagina without requiring use of a speculum until the tip 21 of the device 100 naturally stops at the cervix while the second end 22 of the housing 20 remains outside the vagina. The number of holes 23 at the tip 21 will thus be exposed to the CVF present at the cervix, the CVF being then adjacent and exterior to the tip 21. When the device 100 is in place in the vagina during use, collection of CVF may be performed by grasping the housing or housing 20 with one hand, and rotating the probe 10 (via the cap 50 if such is provided) with another hand relative to the housing in the specific direction that will draw fluid along the screw-like structure 40 to the swab 30. Appreciably, the length of the housing 20 should allow a sufficient part of the housing 20 to remain outside the vagina when the device 100 has been fully inserted in order to allow the housing 20 to be grasped by two or three fingers and a thumb and kept stationary while the probe 10 is rotated relative to the housing 20. To facilitate keeping a stationary hold on the housing 20 during rotation of the probe 10, an exterior surface of the housing 20, at least adjacent the second end 22 of the housing 20, may be provided with grip-enhancing structures such as raised lines 28 as shown in FIG. 13 or even protrusions or wing-like structures (not shown) to improve hand-grip on the housing 20.

After a certain number of rotations, preferably a few complete rotations, the device 100 can be withdrawn and the number of holes 23 at the cotton end or tip 21 of the housing 20 may be sealed with tape for transport to a laboratory for analysis of the collected CVF. Alternatively, the whole device 100 can be placed in a biohazard bag for transport without further manipulation. The biological material collected on the swab 30 is safely protected within the housing 20 throughout the transportation process.

Notably, the device 100 is readily insertable into the vaginal cavity without the need for a speculum as it is slim, similar to a tampon, preferably having a diameter of around only 11 mm. Hence it is likely to be much more comfortable than a vaginal speculum and be less invasive. The housing 20 protects the absorbent swab 30 from contamination during insertion and also protects the swab 30 from contamination or loss of material during removal. As the device 100 is easy to use, it is therefore possible for a patient to perform the swab by herself, further reducing any discomfort one may experience. If the biological marker for analysis is stable, sample collection using this device 100 may be done by the patient at home, and the sample posted to the laboratory for analysis.

In the analysis laboratory, the probe 10 can be removed from the housing 20 and preferably inserted into a typical 15 mL centrifuge tube (not shown). Buffers can be added to the centrifuge tube, and if the probe 10 is provided with a cap 50, the cap 50 can preferably be snapped off from the probe 10 at this stage. The probe 10 can then be sealed within the centrifuge tube. In addition or alternative to the snap-fit connection provided between the cap 50 and the probe 10, the probe 10 may be provided with a breakable portion (not shown) located between the fluid-absorbent swab 30 and the second end 12 of the probe 10 to allow the probe 10 to be broken at the breakable portion and thereby shortened to a length to allow the entire shortened probe 10 to be sealed within the centrifuge tube. This facilitates ease of handling by laboratory staff and reduces possibility of cross contamination. By matching patient labels placed on the housing 20 and the centrifuge tube, identification of the sample can be maintained. In an exemplary embodiment, the breakable portion may have a smaller cross-sectional area than other parts of the probe 10, or the breakable portion may comprise a snap-fit connection between two portions of the probe 10. After the probe 10 has been sealed within the centrifuge tube with buffers, the centrifuge tube is agitated to allow the buffer to remove the biological material from the cotton absorbent swab 30 on the probe 10. The centrifuge tube can then be spun to collect all the liquid material at the bottom of the centrifuge tube and the probe 10 can be discarded. The liquid material is then analysed according to the test ordered.

The presently disclosed device 100 thus improves collection of CVF via the vagina cavity such that the device is unobstructed by the vaginal wall. Summarily, the device consists of two structures. The primary structure of the device 100 is a sterile plastic probe 10 comprising a fluid-absorbent swab 30 that is similar in function to current commercially available vaginal swabs. The second structure forms an empty housing 20 for the probe.

The presently disclosed device 100 addresses all the issues facing the current collection procedure of using a speculum and swab. The device 100 is less intrusive than a speculum, and no more invasive than a tampon applicator. The sample collected is also protected by the housing 20 and much less likely to be affected by contamination. The device 100 is also easier to use and will shorten the time required to collect the sample. It is envisaged that a patient may be taught to use the device 100 and would be able to collect her sample at her convenience. The cost of the device is unlikely to be higher than the current requirement for two medical devices for the same procedure. It would cut down the logistical need to have both the speculum and swab to be available and reduce the cost of both items down to a single item.

As all parts of the device 100 with the exception of the fluid-absorbent swab 30 can be made of one or more plastics materials commonly used in the manufacture of other medical devices, the device 100 is kept accessible to current manufacturing methods for other plastics medical devices, without the need for the development of new manufacturing technologies or methods. In this way, the device 100 is kept easy to manufacture, assemble, package and sterilise. This would keep costs down, enabling the device to be used in a public health setting for screening purposes, and keeping the cost of the device 100 to within a reasonable amount for a single use device.

The present device 100 thus provides an elegant solution to CVF collection without any moving parts for the housing 20 which is the only part that comes into contact with the patient, as the probe 10 or swab 30 do not protrude beyond the housing 20 when inside the vagina. Using the device 100, the chances of an injury for the patient is much reduced. The present device 100 also removes any guesswork as it comes to a natural stopping point within the body during insertion for sample collection. This avoids the possibility of a wrong sample being collected and wasting time in obtaining a diagnosis. In addition, contamination of the swab during withdrawal is avoided as the swab 30 containing the collected fluid always remains fully within the housing 20 during withdrawal of the device 100 including swab 30 from the patient.

The usage of the device 100 is wide ranging and would be used in every single case whereby CVF collection is performed. This may be done for specific circumstances, such as detecting biomarkers for preterm delivery, or for screening programmes. As CVF collection using this device is much less intrusive and embarrassing for patients compared to currently available methods, any screening programmes involving the use of the new device would likely be successful in participation in such screening programmes. Thus, at the national level, healthcare savings may be more substantial from various successful screening programmes. Patients would also be more likely to consent to an increased surveillance, allowing a pickup of healthcare concerns at an earlier stage.

Whilst there has been described in the foregoing description exemplary embodiments of the present invention, it will be understood by those skilled in the technology concerned that many variations and combination in details of design, construction and/or operation may be made without departing from the present invention.

8

What is claimed is:

1. A cervicovaginal fluid collection device comprising:
a tubular housing, a first end of the housing comprising an enclosed tip and a number of through holes provided at the enclosed tip;
a probe provided within the housing, a first end of the probe provided with a screw-like structure, the screw-like structure having a sliding fit with an inner bore of the housing, at least a first end of the screw-like structure provided at the enclosed tip of the housing; and
a fluid-absorbing swab provided on the probe within the housing adjacent a second end of the screw-like structure to absorb fluid drawn into the housing;
wherein rotation of the screw-like structure relative to the housing draws fluid that is adjacent and exterior to the enclosed tip of the housing into the housing through at least one of the through holes; and
wherein fluid drawn into the housing is absorbed by the fluid-absorbing swab.

2. The device of claim 1, wherein the screw-like structure comprises a helical structure wrapped around a central shaft.

3. The device of claim 2, wherein crests of the helical structure form a fluid-seal with the inner bore of the housing.

4. The device of claim 1, wherein the enclosed tip has a rounded configuration.

5. The device of claim 1, wherein the probe is removable from the housing and insertable into a conventional centrifuge tube to allow collection of a cervicovaginal fluid from the fluid-absorbing swab into the centrifuge tube.

6. The device of claim 5, wherein the device is configured to provide the probe to be broken between the fluid-absorbent swab and a second end of the probe to shorten the probe to allow complete insertion and sealing of the shortened probe within the conventional centrifuge tube.

7. The device of claim 1, further comprising a cap in fixed connection with a second end of the probe, the cap provided outside a second end of the housing to facilitate rotation of the probe to rotate the screw-like structure relative to the housing.

8. The device of claim 7, wherein the fixed connection comprises a snap-fit joint allowing the cap to be detached from the second end of the probe.

9. The device of claim 7, wherein the cap encloses the second end of the housing and is in rotatable engagement with the housing.

10. The device of claim 9, wherein the screw-like structure comprises a helical structure wrapped around a central shaft and wherein the cap and the housing are configured to allow the rotatable engagement in only a specific direction dependent on direction of twist of the helical structure around the central shaft.

11. The device of claim 10, wherein the second end of the housing comprises a lip having a number of angled teeth to serve as a ratchet and wherein an inner surface of a cylindrical wall of the cap is provided with a number of angled protrusions to serve as pawls that engage the ratchet.

12. The device of claim 7, wherein the cap comprises a number of protruding stops provided on an outer surface of a cylindrical wall of the cap.

13. The device of claim 7, wherein the cap is provided with an extension cup offset from a main body of the cap enclosing the second end of the housing.

14. The device of claim 8, wherein the cap encloses the second end of the housing and is in rotatable engagement with the housing.

* * * * *